(12) United States Patent
Von Mangoldt et al.

(10) Patent No.: US 11,813,155 B2
(45) Date of Patent: *Nov. 14, 2023

(54) MEDICAL DEVICE FOR EMBOLIC PROTECTION

(71) Applicant: PROTEMBIS GMBH, Aachen (DE)

(72) Inventors: Karl Von Mangoldt, Cologne (DE); Conrad Rasmus, Berlin (DE); Victor Alfonso Jiménez Diaz, Vigo Pontevedra (ES); Carlos Maria Diaz Lopez, Vigo Pontevedra (ES)

(73) Assignee: PROTEMBIS GMBH, Aachen (DE)

( * ) Notice: Subject to any disclaimer, the term of this patent is extended or adjusted under 35 U.S.C. 154(b) by 459 days.

This patent is subject to a terminal disclaimer.

(21) Appl. No.: 16/865,724

(22) Filed: May 4, 2020

(65) Prior Publication Data

US 2020/0261204 A1    Aug. 20, 2020

Related U.S. Application Data

(63) Continuation of application No. 15/029,578, filed as application No. PCT/EP2014/071944 on Oct. 14, 2014, now Pat. No. 10,675,139.

(30) Foreign Application Priority Data

Oct. 14, 2013   (EP) ..................................... 13188522

(51) Int. Cl.
   *A61F 2/01* (2006.01)
(52) U.S. Cl.
   CPC ................. *A61F 2/01* (2013.01); *A61F 2/011* (2020.05); *A61F 2002/016* (2013.01);
   (Continued)

(58) Field of Classification Search
   CPC ................ A61F 2/013; A61F 2002/016; A61F 2230/0008; A61F 2230/0093;
   (Continued)

(56) References Cited

U.S. PATENT DOCUMENTS 5,836,868 A   11/1998  Ressemann et al.
6,245,087 B1  6/2001   Addis
(Continued)

FOREIGN PATENT DOCUMENTS

EP   2337521 B1   6/2011
EP   2732794 A1   5/2014
(Continued)

OTHER PUBLICATIONS

Notice of Reasons for Refusal issued by the Japanese Patent Office for Japanese Patent Application No. 2020-126122 dated May 28, 2021, 14 pages.
(Continued)

*Primary Examiner* — Kelly J Bekker
*Assistant Examiner* — Mohammed S Adam
(74) *Attorney, Agent, or Firm* — Sean Mellino

(57) ABSTRACT

Medical device for embolic protection in an aortic arch, comprising a catheter having a shaft and a distal end portion of the shaft, an expandable embolic protection device having a filter membrane and a frame. The frame comprises a frame loop and an elongated frame shaft having a distal end portion connected to the frame loop in a connection point, in its expanded state the frame loop spans said filter membrane and bending means to bend the distal end portion of the catheter and/or the distal end portion of the frame shaft. The medical device comprises a protective state in which the distal end portion of the catheter is bent, the embolic protection device is expanded, the frame shaft extends in a longitudinal direction of the bent distal end portion and the
(Continued)

expanded frame loop being completely positioned distally of the connection point.

13 Claims, 12 Drawing Sheets

(52) U.S. Cl.
 CPC ............ *A61F 2230/0008* (2013.01); *A61F 2230/0069* (2013.01); *A61F 2230/0093* (2013.01); *A61F 2250/0036* (2013.01); *A61F 2250/0059* (2013.01)

(58) Field of Classification Search
 CPC ...... A61F 2250/0036; A61F 2250/0059; A61F 2002/011
 See application file for complete search history.

(56) References Cited

U.S. PATENT DOCUMENTS

| | | | |
|---|---|---|---|
| 6,258,120 | B1 | 7/2001 | McKenzie et al. |
| 6,361,545 | B1 | 3/2002 | Macoviak et al. |
| 7,163,549 | B2 | 1/2007 | Crank et al. |
| 8,968,354 | B2 * | 3/2015 | Wang ............... A61F 2/013 606/200 |
| 2004/0215167 | A1 | 10/2004 | Belson |
| 2006/0161241 | A1 | 7/2006 | Barbut et al. |
| 2008/0065145 | A1 | 3/2008 | Carpenter |
| 2008/0208245 | A1 | 8/2008 | Hoffman |
| 2010/0211095 | A1 | 8/2010 | Carpenter |
| 2012/0172915 | A1 | 7/2012 | Fifer et al. |
| 2012/0172916 | A1 | 7/2012 | Fifer et al. |
| 2013/0103075 | A1 | 4/2013 | Wang et al. |
| 2013/0218194 | A1 * | 8/2013 | Jonsson ........... A61B 17/12036 606/200 |

FOREIGN PATENT DOCUMENTS

| | | |
|---|---|---|
| JP | 2003-521970 A | 7/2003 |
| JP | 2008543497 | 12/2008 |
| JP | 2012-501704 A | 1/2012 |
| WO | 2001017457 | 3/2001 |
| WO | 2005/009214 A2 | 2/2005 |
| WO | 2005/009214 A3 | 2/2005 |
| WO | 2006/076505 A2 | 7/2006 |
| WO | 2007001902 | 1/2007 |
| WO | 2010/026240 A1 | 3/2010 |
| WO | 2013/063203 A1 | 5/2013 |

OTHER PUBLICATIONS

International Search Report dated Nov. 13, 2014 for International Application No. PCT/EP2014/071944.
International Preliminary Report on Patentability and Written Opinion of the International Searching Authority dated Apr. 19, 2016 for International Application No. PCT/EP2014/071944.
Printout of website http://www.keystoneheart.com/products accessed Aug. 31, 2016.
Communication pursuant to Article 94(3) EPC from the European Patent Office dated Dec. 21, 2016 for corresponding EP Application No. 13188522.0.
Communication pursuant to Article 94(3) EPC from the European Patent Office dated Dec. 5, 2018 for corresponding EP Application No. 13188522.0.
Office Action from the Japanese Patent Office dated Jul. 19, 2019 for corresponding JP Patent Application No. 2018-183804.
Office Action from the Israeli Patent Office dated Sep. 5, 2019 for corresponding IL Patent Application No. 245049.
Office Action from the Israeli Patent Office dated Aug. 6, 2020 for corresponding IL Patent Application No. 245049.
Response to corresponding Japanese Office Action dated Jun. 8, 2021 and Amended Claims for Japanese Patent Application No. 2020-126122.

* cited by examiner

MEDICAL DEVICE FOR EMBOLIC PROTECTION

CROSS-REFERENCE TO RELATED APPLICATIONS

This application is a continuation of U.S. application Ser. No. 15/029,578 entitled MEDICAL DEVICE FOR EMBOLIC PROTECTION, filed on Apr. 14, 2016, which is a 371 National Stage application of International Application No. PCT/EP2014/071944 filed on Oct. 14, 2014, which claims priority of European Patent (EP) application Serial Number 13188522.0 filed on Oct. 14, 2013, each of which is incorporated herein by reference in its entirety.

BACKGROUND OF THE INVENTION

Field of the Invention

The invention pertains in general to the field of medical devices and procedures for applying such medical devices. Most particularly, the present invention relates to a device and a method for providing embolic protection to a patient's aortic arch vessels by diverting and/or capturing solid particles during cardiac surgery and interventional cardiology procedures.

Description of the Prior Art

Atherosclerosis and thromboembolic disorders, such as stroke, pulmonary embolism, peripheral thrombosis, and the like, affect a large amount of population. These diseases are a major cause of morbidity and mortality in the United States, Europe and throughout the world. The extent of damage is usually systemic, and atherosclerosis may display a diffuse pattern, affecting the aorta, the coronary, carotid, and renal arteries among others.

Transcatheter procedures are being increasingly used to treat a wide variety of cardiac and vascular surgical problems due to its less invasiveness compared to open-heart surgery, but cerebral embolism is a well-known and feared complication that affects patients undergoing not only cardiac surgery and cardiopulmonary bypass, but also patients treated with catheter-based interventional cardiology and electrophysiology procedures.

Periprocedural stroke constitute the most debilitating complication from the patient's perspective, associated with a high rate of morbidity and mortality. Although the overall rate of clinical stroke after heart catheterization is low, ranging from 0.2% to 0.5% in percutaneous coronary intervention (PCI), the incidence of microembolic signal detected by transcraneal Doppler and cerebral infarct by cranial magnetic resonance rises as high as 84% after Transcatheter Aortic Valve Implantation (TAVI), 15% after PCI, 22% after retrograde catheterization in severe aortic stenosis, and 5-6% after radiofrequency catheter ablation.

During the performance of any endovascular or surgical procedure involving the passage of catheters across the aortic arch, air embolism, thrombus formation in the catheter or on its surface, or the dislodgement of plaque or other material by surgical or catheter manipulations can occur, and this debris can embolize into the carotid vessels resulting in neuropsychological deficits, stroke, or even death.

Patients with coronary artery disease more frequently have severe atheroma in the descending aorta and aortic arch than patients without coronary artery disease. Also, the aortic arch and the aortic valve are recognized as sources of embolic material, and the presence of atheroma in the aortic arch is an independent risk factor for recurrent stroke. Prevention of cerebral embolism during these procedures would benefit and improve the outcome of a large population of patients at high risk of thromboembolic events.

Some devices have been developed with the purpose of protecting the brain vasculature against embolic particles. The devices comprise filters or emboli deflectors. The main problems described with intravascular filtering devices include the placement of the filter in some segments within the carotid arteries with atherosclerotic plaques, the difficulty in its placement and retrieval, mainly during the recapture of the filter to withdraw the emboli from the body that can be difficult depending upon the volume of entrapped emboli, and the reduced perfusion through the filter due to the captured emboli, with the possibility of complete filling of the filter, obstructing the cerebral circulation during the procedure.

Patients requiring cardiac or aortic arch procedures are high risk candidates for having carotid disease. These procedures simultaneously place both carotid arteries at risk for emboli. The chance of causing a stroke by selectively cannulating both carotid arteries, navigating a catheter within the artery and placement of a protective device is high, and the time and skill necessary to be exercised has also contributed to the lack of general application and use, despite of the high stroke risk during cardiac and aortic arch procedures.

There are some medical devices designed to protect both carotid arteries at the same time by placing a filter inside the artery lumen.

US 2012/0172916A1 discloses a 6 French catheter designed to capture and remove debris dislodged during intravascular procedures. This device delivers two embolic filters, one to the brachiocephalic artery, and a second to the left common carotid artery. Both filters are recaptured into the catheter at the end of the procedure, along with captured debris, and removed from the patient. Although this device is compatible with a low profile access port, its use is limited due to the fact that most of patients selected for transcatheter valve procedures are of advanced age and the incidence of severe tortuosity and calcification of the right subclavian artery is very high in these patients, preventing proper navigation and delivery of the device in the artery at the desired position.

A similar device, the ValveNet™ Filtration Catheter by Lumen Biomedical Inc. provides filtering of blood flow from the aorta to the left carotid artery and the right carotid artery by placing filter baskets on them, allowing removal of embolic material. Although this device is compatible with variable arch anatomies and it does not use a filter recovery step, it has certain disadvantages such as the need of a 7 French access port which is too large for being used by the radial artery in the majority of patients. Furthermore, both devices exhibit the same and more important disadvantage: the need to selectively cannulate both carotid arteries with a guide wire extending between the brachiocephalic artery to the right and left carotid arteries, crossing the aortic arch, bringing unavoidably intravascular handling. Thus, the risk for iatrogenic caused damage to the carotid artery walls or plaque dislodgement with embolization to the brain is important, knowing that a significant proportion of patients in which this device meant to be used, has variable degrees of carotid atherosclerotic disease.

Only a small number of devices have recently been developed which are designed to protect both carotid arteries at the same time without placing a protective device on its lumen.

US 2008/0065145 discloses a deflector extending over the ostia of the brachiocephalic artery and left carotid artery. The device is inserted percutaneously and placed by means of a catheter, using a 6 French sheath mainly through an artery of the arm or also by the femoral artery, into the brachiocephalic artery and the right subclavian artery. The use of a guide wire arranged extending between the aortic arch and the brachiocephalic artery leads to unfavorable intravascular handling. Thus a risk for iatrogenic caused embolization to the right carotid artery or damage to the vessel wall is present. Furthermore, there is no fixing mechanism or support mechanism that holds the device in place during the procedure, so that with the constant aortic blood flow and the passage of catheters through the aortic arch, the device can be hooked or displaced.

In U.S. Pat. No. 6,361,545 (Cardeon Corp.) a perfusion filter catheter is disclosed. The device has an elongated cone shape, and is adapted to deploy an expandable fine filter mesh for capturing macroemboli and microemboli during heart surgery and cardiopulmonary bypass. The device is inserted via the femoral artery, subclavian artery, or by transaortic cut-off, and it's deployed in the ascending aorta to protect at least one side branch vessel from embolism. Potential problems of this device include the necessity to use a big size access port and introductory sheath, making its use nearly impossible percutaneously through the radial artery. Also, by covering the origin of the side branch of the aortic arch vessels, precludes the use of both right and left subclavian artery, widely used for placement of catheters and other devices during TAVI and other cardiovascular invasive procedures. Moreover, as its design includes the pass of blood flow only through the perfusion lumen; this could be substantially hindered through the aortic arch, thus causing possible periods of cerebral hypoperfusion during the procedure.

The Emboline device, disclosed in US 2004/0215167, has a substantially flat panel of filter mesh material made of Nitinol® or other metal or polymer, and supported on a wire frame or an expandable tubular structure. The device is compressed to a small diameter for insertion into a patient's aorta and then expanded within the aorta with the filter mesh material positioned to allow blood to enter side branch vessels connected to the aorta and to prevent embolic material from entering the side branch vessels. The device is deployed and left in place for long-term protection. Alternatively, the device may be compressed and withdrawn from the aorta. This device provides complete protection to the cerebral vascular bed of possible emboli during cardiovascular procedures. The most important drawbacks of this device are that using a big size access port and introductory sheath, restricts its use strictly to the femoral approach, which in turn is occupied by the large catheters of the endovascular procedures, increasing the risk of vascular complications at the femoral access site. Also, by covering the origin of the side branch of the aortic arch vessels precludes the use of both right and left subclavian artery. Moreover, the device may be difficult to extract from the aortic arch, as a stent like design is devised for permanent implantation and removing a stent may harm the implantation site. In addition, the device may be pressed against or into the ostia regions of the side branch vessels, and due the characteristics of the mesh material, similar to a stent device, plaque dislodgement can be washed along the side branch vessels as debris constituting embolic material.

The embolic device disclosed in U.S. Pat. No. 6,258,120 is designed for use in open heart surgery during cardiopulmonary bypass by diverting emboli away from the carotid arteries in the aorta. The device is a filtering screen inserted directly into the ascending aorta immediately beyond the aortic valve, filtering all the blood exiting the left ventricle and bypass machine prior to allowing it to pass to the downstream circulation. Limitations of this device include its applicability mostly to open heart surgery and in some cases of cardiac procedures by direct aortic approach, excluding its use in the vast majority of endovascular procedures requiring cerebral embolic protection. Also, it's not easy to use, the device most be secured to the lumen of the aorta through some mechanism including sutures, surgical clips, hooks, adhesive materials, substantially rigid sleeves, or frictional engagement, making difficult to accomplish by transvascular access. Because the device completely spans the aorta, the passage of catheters and wires coming from others vascular accesses through the aortic arch is not possible.

The Triguard™ Device by Keystone Heart Ltd uses a Nitinol® frame and mesh designed to cover all aortic cerebral branches and deflect embolic debris during cardiovascular procedures. The device is introduced by a 9 French femoral artery access port. This device requires feelers pressing against the wall of the aortic arch. Therefore, the device can damage the vessel walls or can get hooked with catheters or wires during its passage into the aortic arch. Also, the device has a stabilizer into the brachiocephalic trunk that can damage the vessel wall. Moreover, due to its design and the need of 9 French sheaths, its introduction by the radial artery and the passage of catheters and wires coming from other arterial vascular accesses besides the femoral artery is not possible.

In EP 2,337,521 B1 an embolic protection device and method of use is disclosed. The device is a collapsible flat panel devised for temporary transvascular delivery through the left subclavian artery and extending over the ostia of the side branch vessels of the aortic arch. The device has two support members or petals, one is shaped in apposition to tissue of a vessel wall portion of the aortic arch and the other is shaped in apposition to tissue of a vessel wall portion of the ascending aorta. The mesh is non-tubular or may have a flat umbrella shape. The mesh is positioned at a distance from the ostia regions of the side branch vessels of the aortic arch. The known device leaves a space between the mesh, the ostia of the side branch vessels and the lateral walls of the aortic arch, causing incomplete sealing and protection of the ostia of the side branch vessels, and allowing the passage of microembolic particles to the brain. Furthermore, the supporting member can damage the aortic arch wall during deployment and positioning of the protective device, or by an unintentional movement or shove by the catheters passing through the aortic arch during the procedure. Also, the device will have to be very large in order to cover the ostia of the three side branch vessels of the aortic arch, making it voluminous, not easy to handle within the aortic arch, and unlikely to have a low profile in order to use the radial artery as vascular access route. Moreover, the device acts just like a deflector and does not collect debris.

Therefore, existing cerebral embolic protection devices have deficiencies, including: difficult to handle and to position in a vessel or two vessels, they may cause damage to the arterial walls and potentially cause an embolic event themselves, they may cause damage to the walls of the ascending aorta, descending aorta and aortic arch, which may lead to serious consequences, visualization of the protective device may impair visualization of other components used during concurrent interventional procedures.

SUMMARY OF THE PRESENT INVENTION

The technical problem of the invention is to provide an improved embolic protection device which allows performing transluminal or surgical procedures in the vicinity of the heart without the shortcoming of the known devices.

The problem is solved by a medical device for embolic protection having the features of claim 1. Preferred embodiments are subject matter of the dependent claims.

The medical device according to the invention is suited for embolic protection in the aortic arch. The medical device comprises a catheter and an expandable embolic protection device which can be forwarded into the aorta of a patient with the help of the catheter. The catheter comprises a catheter shaft. The distal end of the catheter shaft comprises in one possible embodiment of the invention a distal end portion provided with bending means for the distal end portion of the catheter. The distal end portion of the catheter bends under a bending angle with respect to the portion of the catheter shaft which is not bent. The medical device according to the invention is characterized by an expandable embolic protection device. The embolic protection device comprises a filter membrane and a frame. The filter membrane allows a through-going blood flow, but blocks embolic particles. The frame of the embolic protection device comprises a frame loop and an elongated frame shaft. Frame loop and frame shaft are connected to each other in a connection point. In its unexpanded state the embolic protection device is preferably placed entirely within the catheter. In its expanded state the frame loop spans said filter membrane. The distal end portion of the frame shaft may in addition or in alternative be provided with bending means. Just as the bending means of the catheter shaft, also the bending means of the frame shaft are actuated to bend the distal end portion of the frame shaft. By the bending means the frame shaft is bent under a bending angle. The bending of the frame shaft can be supported by additional bending means in the distal end portion of the catheter shaft. It is also possible that bending is achieved by bending means of the frame shaft which also bends a distal end portion of the catheter shaft. The medical device according to the invention has a protective state. In its protective state the distal end portion of the catheter is bent and the embolic protection device is expanded. The configuration of the medical device in its protective state is such that the frame shaft extends in the longitudinal direction of the bent distal end portion; that is the frame shaft extends under the bending angle which is formed between the distal opening of the catheter and the catheter shaft proximal to the distal end portion. Furthermore, the protective state is characterized in that the expanded frame loop being completely positioned distally from said connection point and said frame shaft. In the aortic arch, the expanded frame loop is therefore entirely upstream of the connection point with respect to the flowing direction of the blood. In the alternative, in particular if the catheter is introduced by the right subclavian vessel, the expanded frame loop is entirely downstream of said connection point. One of the effects achieved with the embolic protection device is that the expanded frame loop is not positioned in front of the side branch vessel in which the catheter is positioned. Unlike other devices (Triguard™ and EP 2,337,521 B1), the presence of tongues, stabilizers, feelers, or wings as support members which are in contact with the walls of the aortic arch, and ascending or descending aorta, are not necessary in the device according to the invention, thereby avoiding the possibility of damaging the aorta walls. The fixation and support of the device is also provided by the deflection or bending mechanism of the distal end of the device and/or delivery catheter. The pressure of the blood flowing in the aortic arch presses the membrane against the vessel tissue portion, so that there is no necessity of tensioning and tightening the membrane against the walls of the ascending and descending aorta or aortic arch.

In a preferred embodiment the medical device according to the invention has a filter membrane which in the expanded state of said frame has a concave shape. Preferably the filter membrane has a preformed concave shape. The concave shape allows a filter membrane to partially enter into the side branch vessel and therefore to seal the opening of the side branch vessel more tightly. Unlike the mesh of the other devices which are rigid and made of metal (like Nitinol® of the Triguard™ device; Emboline US 2004/0215167, and EP 2,337,521 B1), or with a flat shape (like polyurethane in US 2008/0065145; or Nitinol® in Triguard™; EP 2,337,521 B1, Emboline US 2004/0215167), the filter membrane of the device according to the invention is pre-shaped to a concave or dished form to provide a better apposition to the tissue of the aortic arch roof, encircling the plurality of the ostia of the aortic side branch vessels inside the aortic arch, covering its entrance with the capability of protruding slightly inside the side branch vessels. In this manner the filter membrane is arranged to separate a first fluid volume of the aortic side branch vessels from a second fluid volume in the aortic arch when the protection unit is positioned in the aortic arch.

The concave shape of the pre-formed filter membrane is supported by a frame in a preferable concave shape. Furthermore, the filter membrane is in a preferred embodiment more flexible in a center region than in a peripheral region closer to the frame. The flexibility can be achieved by an uneven distribution of the thickness of the filter membrane. Unlike other devices, the frame is pre-shaped with a slightly concave form so that it is intentionally bent back to press against the aortic roof wall when it is deployed acquiring the anatomical form of the aortic arch, avoiding to hinder the passage of catheters and devices through the aortic arch, like may happen with the Triguard™ device, Emboline US 2004/0215167, and EP 2,337,521 B 1.

In a further preferred embodiment, a deployable filter device is provided which in its deployed state extends circumferentially around the catheter shaft or said distal end portion of the catheter. The deployable filter device protects the side branch vessel through which the catheter is advanced to the aortic branch. If the catheter is positioned in the right subclavian vessel, the deployable filter device closes the brachiocephalic trunk. If the catheter is forwarded through the left subclavian vessel, the device closes the left subclavian vessel and the left vertebral artery. An additional deployable filter device in combination with the expandable embolic protection device has the advantage that all side branch vessels of the aortic arch are closed for embolic particles while at the same time the filter device and the embolic protection device are easy to handle and control.

The filter membrane of the embolic protection device is preferably a porous membrane. The membrane is made of a polymer material and preferably comprises at least two different portions having a different thickness. The membrane may be heparin coated, coated with other substances or uncoated. Unlike other devices, close contact with the ostium of the side branch vessels and surrounding tissue is intentionally sought with the membrane of the device, as well as slight protrusion of the membrane within the side branch vessels. Due to the atraumatic characteristics of the membrane material, the risk of release any plaque or other debris from there to the brain is minimal, allowing certain movement towards the ostia due to mechanical pressure from inside the aorta arch.

In a preferred embodiment the bendable distal end portion of the catheter has a length of 10 mm to 80 mm, preferably of 20 mm to 60 mm. In a most preferred embodiment the length of the bendable distal end portion is 40 mm to 60 mm.

The membrane is preferably made of Siloxane (PDMS, Poly-dimethyl siloxane)-CH3[Si(CH3)2O]nSi(CH3)3—a polymer with non-sticking properties, hydrophobic, and highly flexible and elastic, and that due its characteristics enable it to go slightly inside the ostia of the side branch vessels, differing from the rigid Nitinol® mesh which crosses in a straight and inflexible manner, the entire length of the aortic arch. The material of the membrane gives the possibility of folding, unfolding and refolding within a low profile catheter.

The technical problem of the invention is also solved by a method of positioning the above mentioned medical device in the aortic arch for embolic protection during transluminal or surgical procedures in the vicinity of the heart.

In a preferred embodiment the method provides embolic protection for the brachiocephalic trunk and left common carotid artery. The preferred method comprises the step of introducing an embolic protection device into the patient's aorta, the embolic protection device comprising an expandable frame supporting a filter membrane. The frame comprises a frame loop to which preferably the filter membrane is connected partially of completely by surrounding a periphery of the frame loop. The frame loop is connected to the frame shaft. The frame loop is configured engaging an interior wall of the aorta to support the embolic protection device within the patient's aorta covering the ostia of the brachiocephalic trunk and left common carotid artery. In a compressed position the embolic protection device has a diameter which fits within the catheter for insertion into the patient's aorta. The method further comprises expanding the embolic protection device to its expanded state within the patient's aorta and allow blood to enter the side branch vessels to prevent embolic material from entering the side branch vessels, wherein the embolic protection device is recaptured into the catheter acquiring a compressed state within the catheter. Due to its method of use and site of placement of the device according to the invention, there is no necessity of entering with a guidewire or with the protection device within the carotid arteries, like for Claret Device patent US 2012/0172916A1, and with ValveNet™ device, avoiding the risk of plaque dislodgement and iatrogenic embolization to the brain.

BRIEF DESCRIPTION OF THE DRAWINGS

Some embodiments of the invention are explained with respect to the enclosed Figures.

DETAILED DESCRIPTION OF THE PRESENT INVENTION

Figure 1:
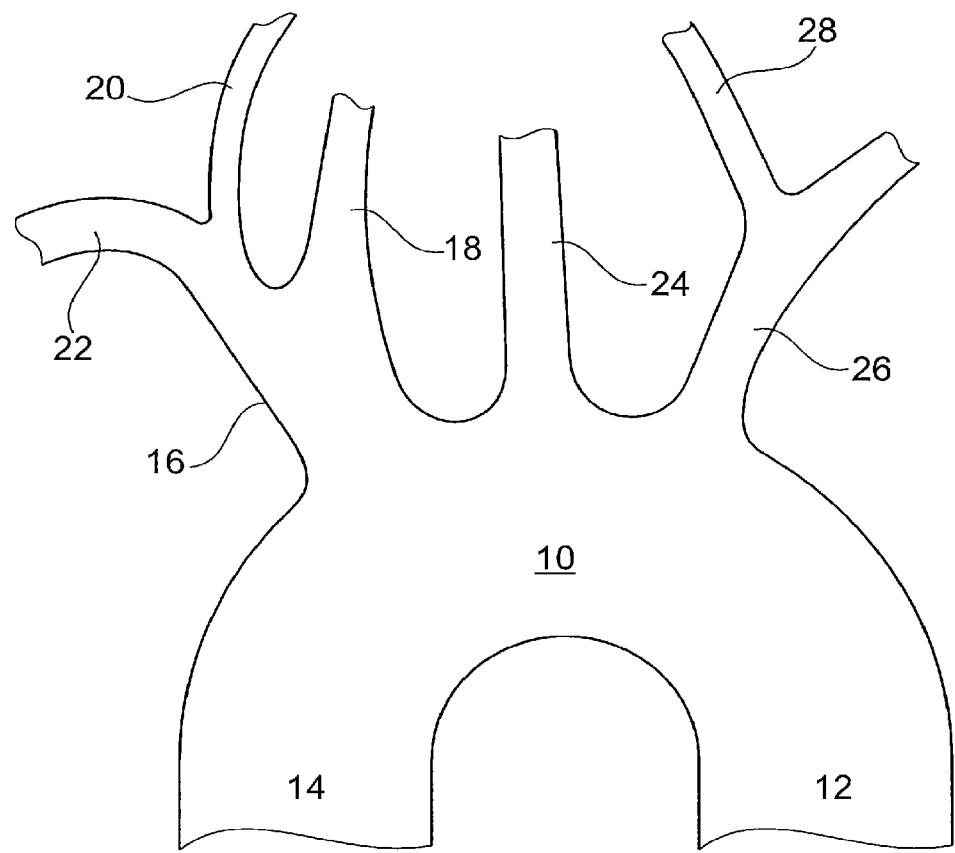
FIG. 1 shows in a schematic drawing the aortic arch and its side branch vessels, FIG. 2a an expandable embolic protection device in a frontal view, FIG. 2b an embolic protection device in a lateral view with the distal portion of the catheter shaft, FIG. 2c the embolic protection device with a detail of the filter membrane in an enlarged view, FIG. 3 a first embodiment of the medical device with the embolic protection device in the desired position covering the ostia of two side branch vessels, FIG. 4 a second embodiment of the medical device comprising a filter in the left subclavian artery, FIG. 5 a third embodiment of the medical device comprising a filter positioned in the brachiocephalic trunk, FIG. 6a the first embodiment of the medical device during left subclavian delivery, FIG. 6b the left subclavian delivery with the embolic protection device expanded into the aortic arch, FIG. 6c the left subclavian delivery according to FIG. 6a and FIG. 6b with a catheter bending, FIG. 6d the left subclavian delivery with the medical device in its protective state, FIG. 6e the left subclavian delivery with the filter membrane re-entering the catheter, FIG. 7a-7e the left subclavian delivery in a perspective view and FIG. 8a-8d a femoral delivery of a fourth embodiment for femoral delivery.

FIG. 1 shows in a schematic drawing of the aortic arch 10 with its descending aorta 12 and ascending aorta 14. The ascending aorta 14 leads directly to the aortic valves and the heart. In the aortic arch 10 there is the brachiocephalic trunk 16 from which the right common carotid artery 18 and the right vertebral artery 20 and the right subclavian artery 22 branches off. Next in the aortic arch is the left common carotid artery 24 which is followed by the left subclavian artery 26. The left vertebral artery 28 branches off from the left subclavian artery 26.

Figure 2A:
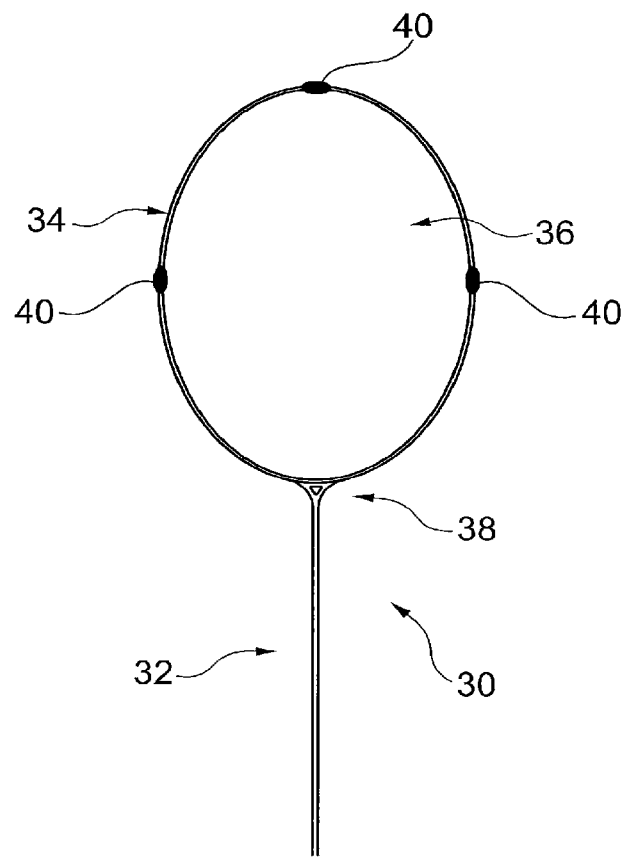

FIG. 2a shows an embolic protection device 30 in its expanded state. The embolic protection device 30 has an elongated frame shaft 32, which is flexible to be bent. Furthermore, the embolic protection device comprises a closed frame loop 34. The frame loop 34 carries the filter membrane 36. Between the frame shaft 32 and the frame loop 34 there is the connection point 38. The connection point 38 may have a triangular shape. Furthermore, the embolic protection device 30 carries three radiopaque markers 40 which allow controlling the orientation of the expanded frame during positioning of the embolic protection device.

Figure 2B:
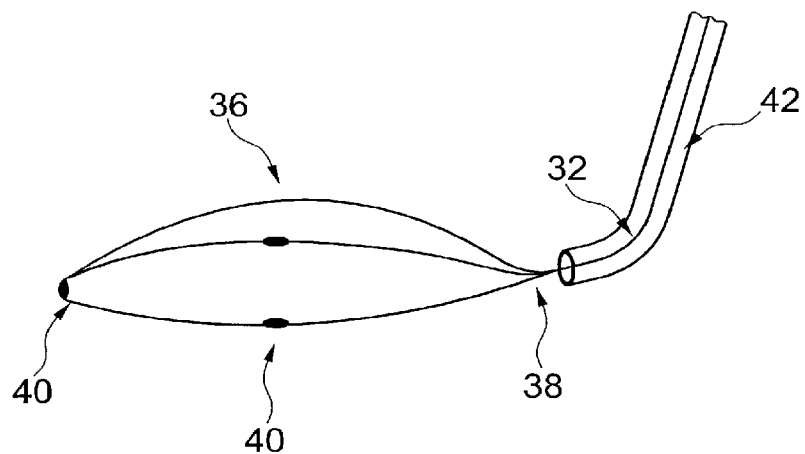

FIG. 2b shows the embolic protection device 30 extending from a bent catheter shaft 42. The frame shaft 32 of the embolic protection device is bent by bending of the catheter shaft 42 at its distal tip. In a different embodiment in addition or in alternative to the bending of the catheter the elongated frame shaft can be provided with bending means. In FIG. 2b it is shown that the filter membrane 36 has a concave shape similar to a spherical calotte.

Figure 2C:
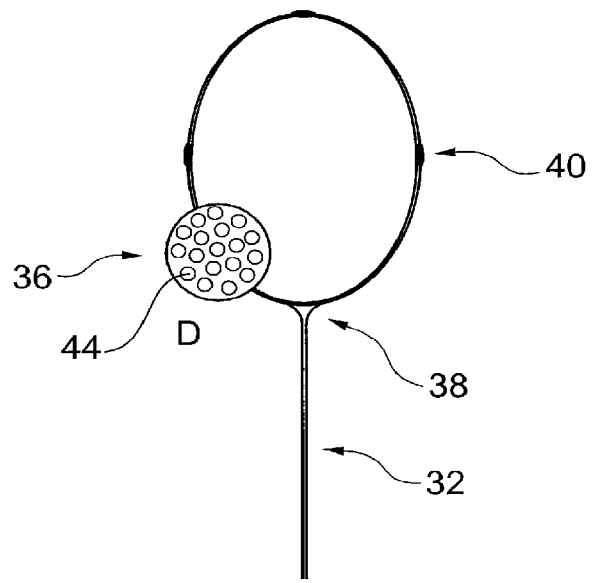

FIG. 2c shows the embolic protection device of FIG. 2a with an enlarged detail D which shows the porous structure of the filter membrane. The porous structure is made of small through-holes 44 in an irregular configuration. The porous structure may also comprise through-holes 44 arranged in a regular configuration. The diameter of the through-holes may either be the same for all through-holes or vary within a predefined range of diameters. The diameter of pores are preferable about 70-90 microns, in particular 80 microns and differ from other devices (Embrella 100 microns, Claret 140 microns, Triguard™ 200 microns), deflecting even small microparticles of critical size away from the cerebral circulation.

Figure 3:
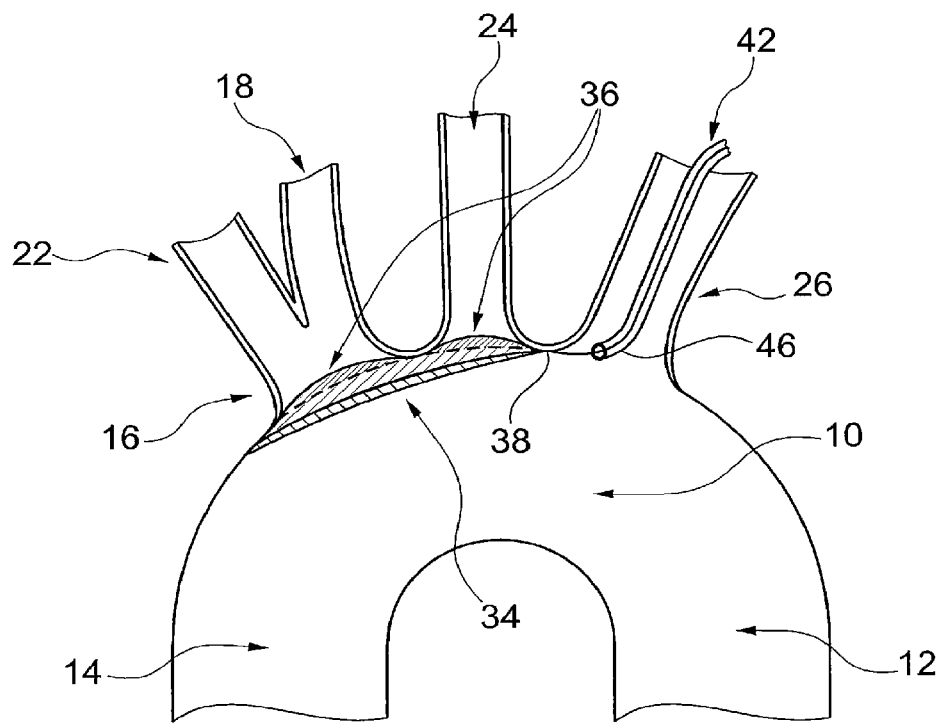

FIG. 3 shows a first embodiment of the invention. The catheter shaft 42 is inserted through an artery of the left arm and enters the aortic arch through the left subclavian artery 26. The expanded filter membrane 36 covers the ostia of the brachiocephalic trunk 16 and the left common carotid artery 24. As can be seen in FIG. 3 the filter material dips into the ostia and has therefore a soft and atraumatic contact with the vessel wall. The filter material also provides a good sealing of the ostia by a close contact to the vessel wall. In order to improve sealing it to the vessel walls is also considered to provide a circumferential band in the filter membrane without any through-holes. The circumferential or peripheral band is preferably provided close to the frame loop. In the preferred embodiment the circumferential band is free of through-holes and brought into close contact with the vessel wall.

The distal end portion 46 of the catheter shaft 42 is bent to point into the direction of the other side branch vessels 16-24. From FIG. 3 it is clear that the frame loop 34 lies entirely on one side of the connection point 38.

Figure 4:
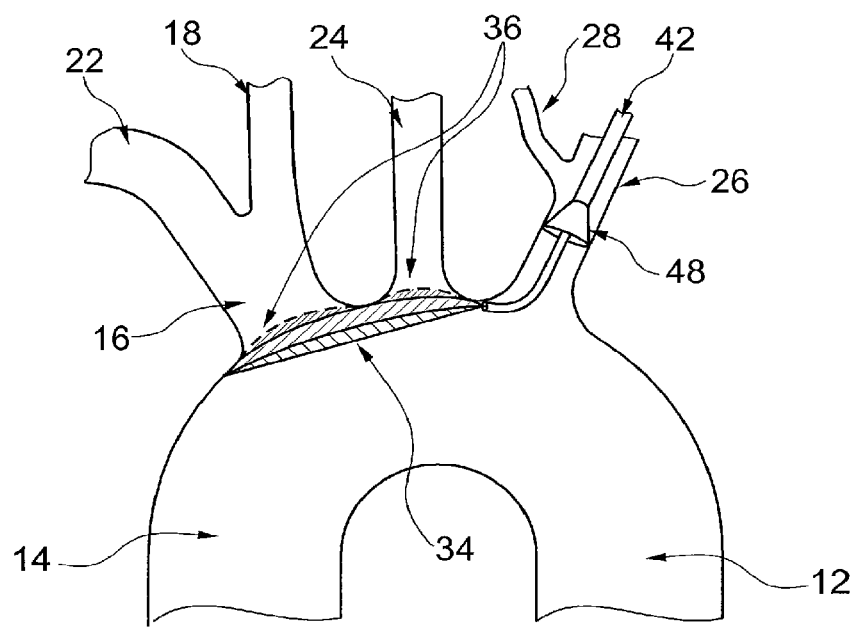

FIG. 4 shows an alternative embodiment with a catheter again placed in the left subclavian artery 26. In this embodiment the catheter shaft 42 is provided with a deployable filter 48. The filter 48 is of a tapered shape with its end open towards the aortic arch. Additionally to the embolic protection provided for the brachiocephalic trunk 16 and the left common carotid artery 24, the left subclavian artery 26 is protected by the deployable filter 48. Besides the mentioned tapered shape it is also possible to use a basket or any other shape suitable to allow a blood flow through the left subclavian artery and to block the subclavian artery for embolic particles.

Figure 5:
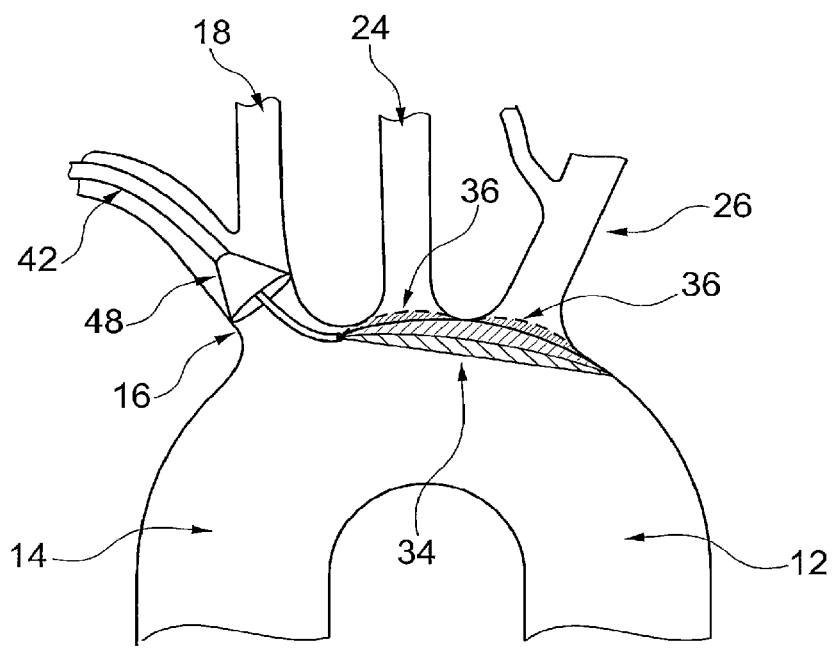

FIG. 5 shows a further embodiment in which the catheter shaft 42 enters the aortic arch 10 through the right subclavian artery 22. In this embodiment the filter 48 is provided within the brachiocephalic trunk 16 to filter a blood stream to the right common carotid artery 18, the right subclavian artery 22 and the other vessels branching off therefrom. Again the filter membrane protects the left common carotid artery 24 and the left subclavian artery 26. The filter membrane 36 dips into the ostium of the vessels 24 and 26.

Figure 6A:
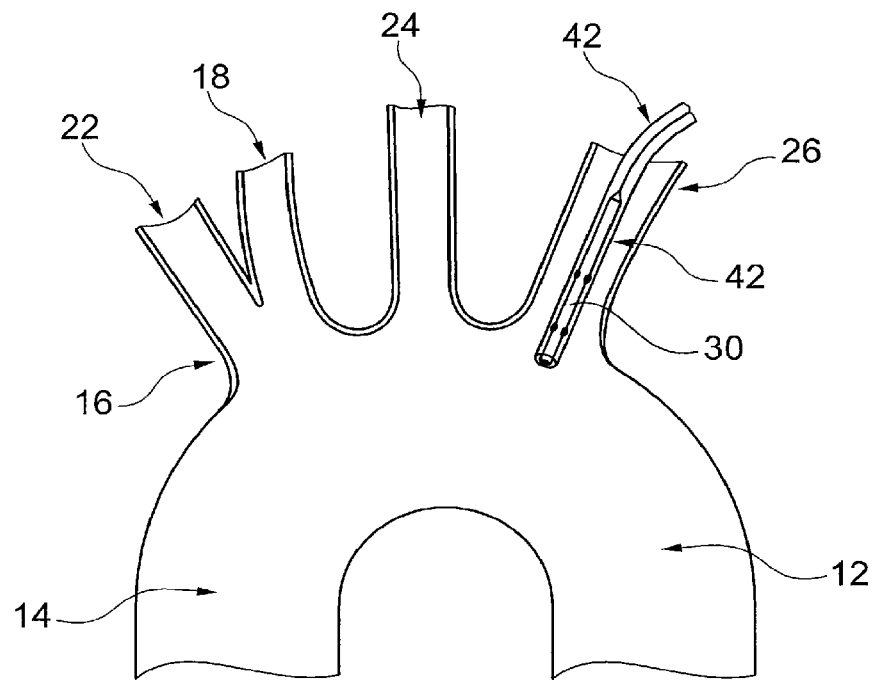
Figure 6B:
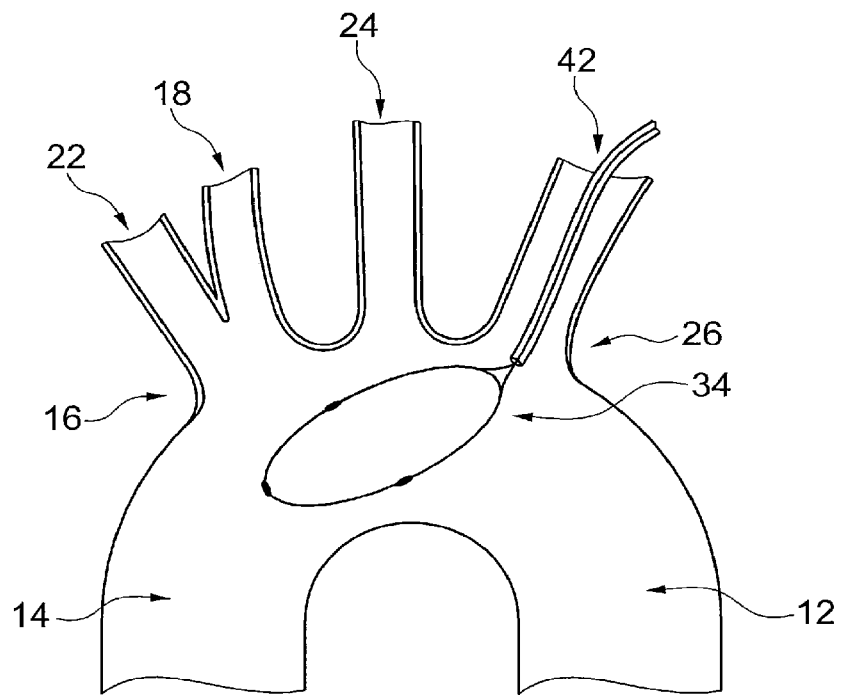
Figure 6C:
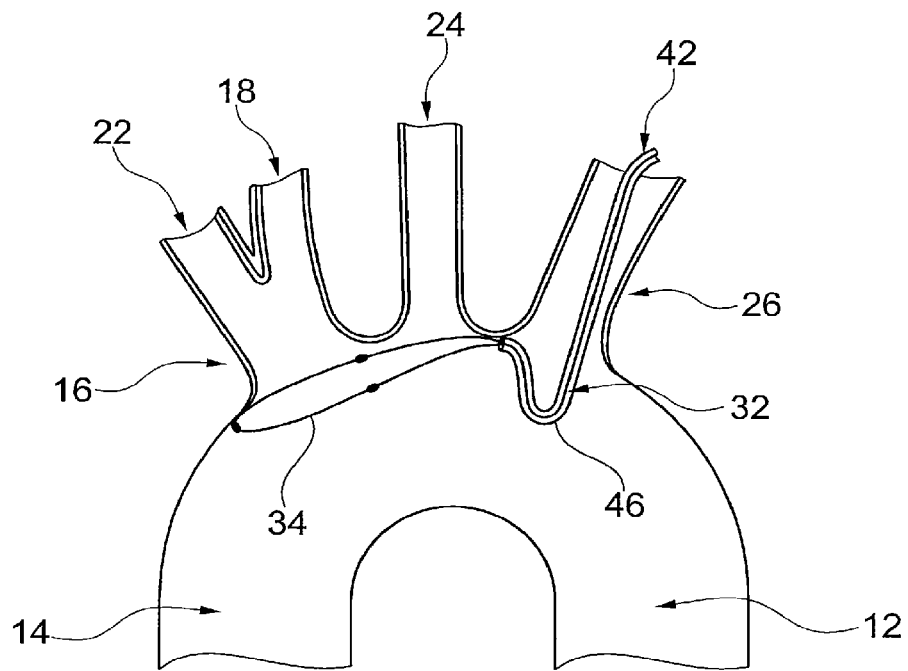
Figure 6D:
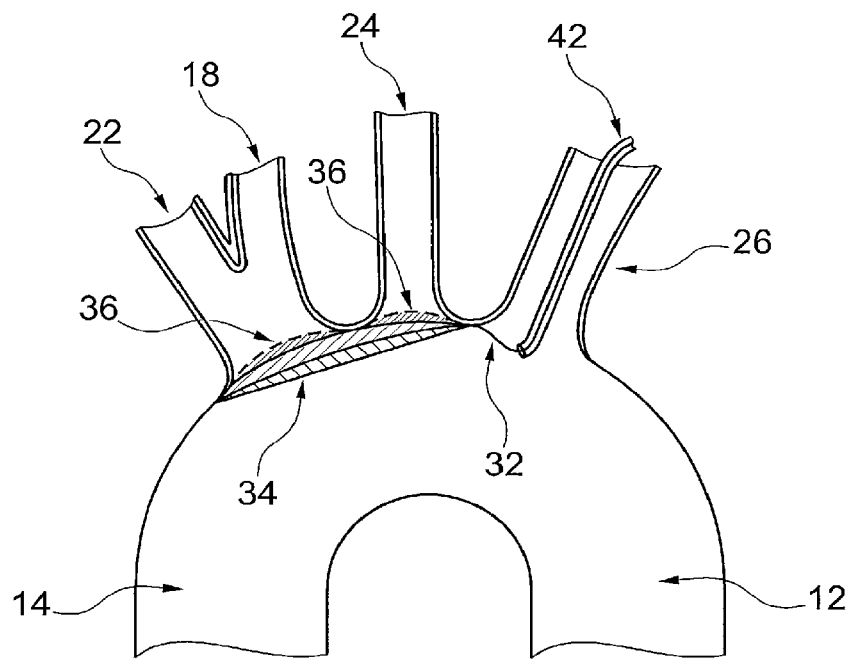
Figure 6E:
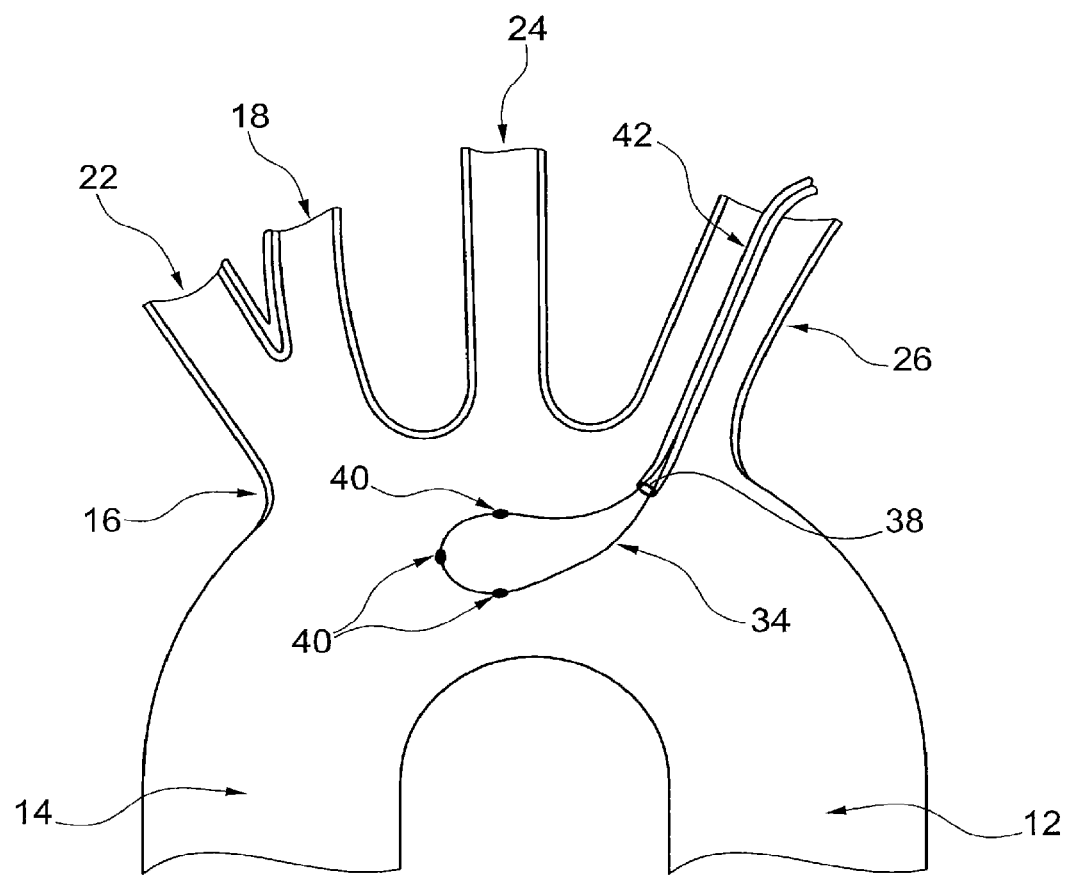
Figure 7A:
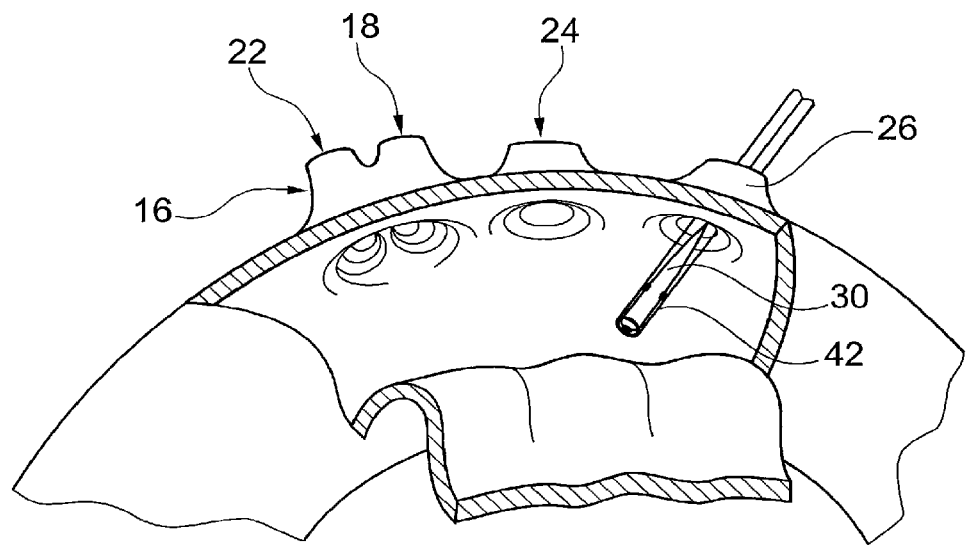

FIGS. 6a to 6e and FIGS. 7a to 7e describe stepwise the positioning of the embolic protection device within the aortic arch 10 through the left subclavian artery 26. FIG. 6a as well as FIG. 7a shows the catheter shaft 42 entering to the aortic arch 10 through the left subclavian artery 26. For a better understanding the catheter 42 is shown transparent so that the embolic protection device 30 is visible in the catheter and in the left subclavian artery 26.

Figure 7B:
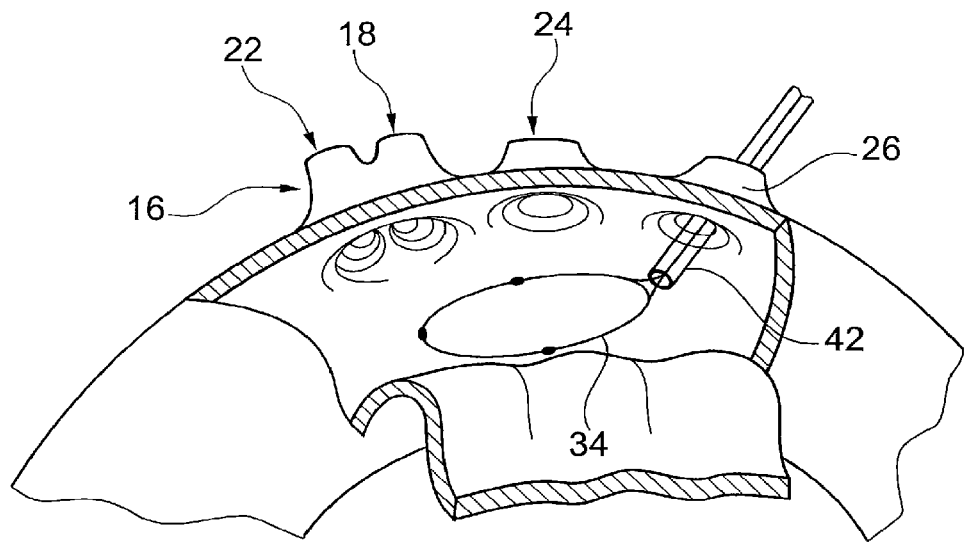

FIG. 6b and FIG. 7b show the embolic protection device 30 in its expanded state after leaving the catheter 42. The frame loop 34 is expanded for example by using a shape-memory material such as Nitinol®.

Figure 7C:
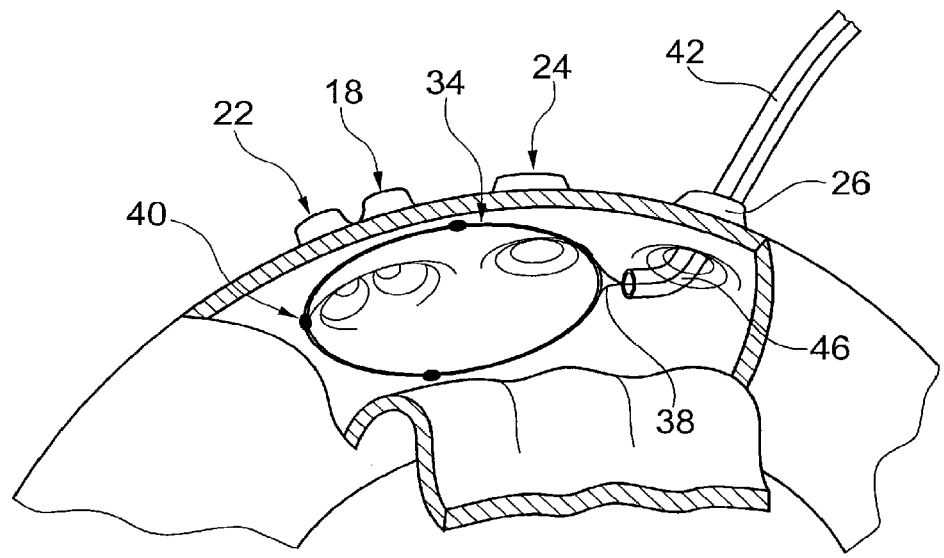
Figure 7D:
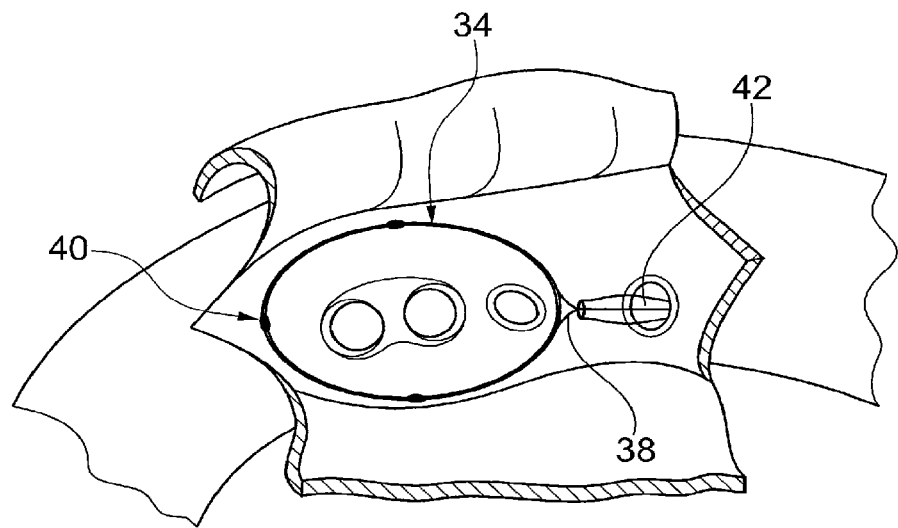

FIGS. 6c and 7c show the approximation of the embolic protection device 34 to the roof of the aortic arch by the bending mechanism 46 of the catheter. In a first step the bending mechanism 46 provides a large bending angle of 60° to 180°, preferable of 0° to 270°. Later on as shown in FIG. 6d and in FIG. 7d the catheter 42 is retracted partly so that the bending angle in particular of the frame shaft 32 is reduced. In FIGS. 6d and 7d the frame 34 has reached its protective position within the aortic arch.

Figure 7E:
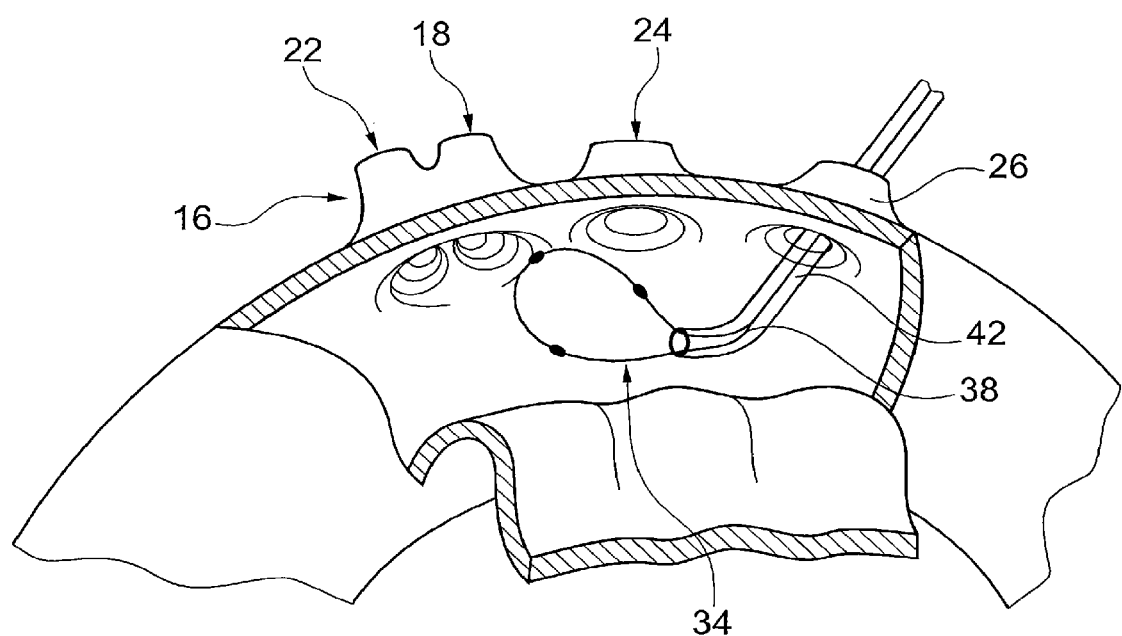

FIGS. 6e and 7e show retracting of the frame into the catheter 42. As shown in FIGS. 6e and 7e the loop folds up after the connection point 38 has re-entered the catheter.

The above described procedure of FIGS. 6 and 7 can of course be carried out with catheter having a tapered filter 48 on its shaft or not.

Figure 8A:
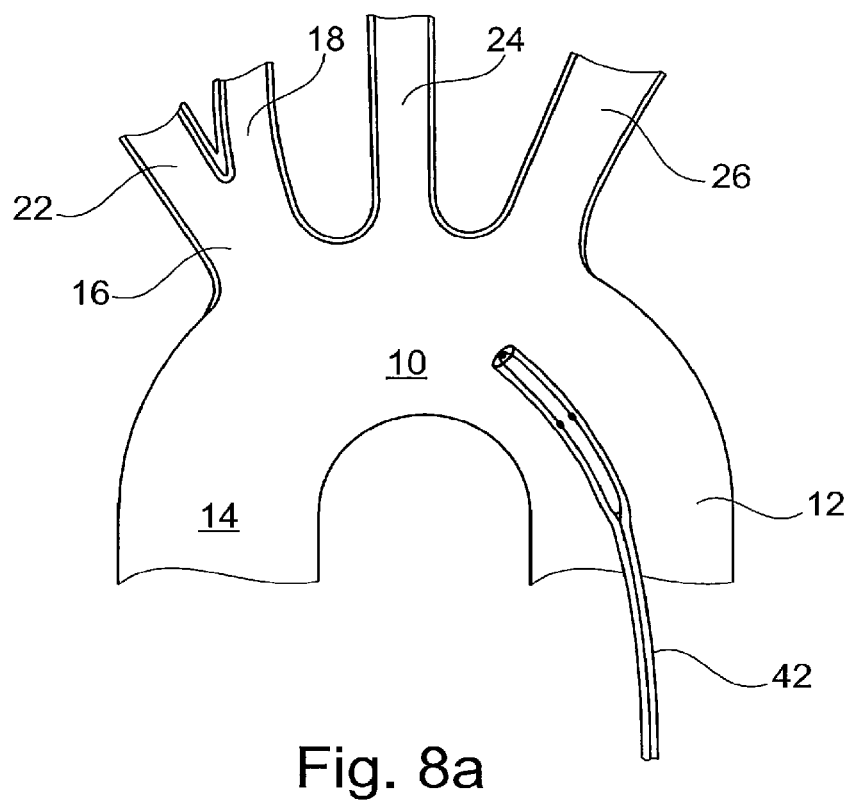
Figure 8B:
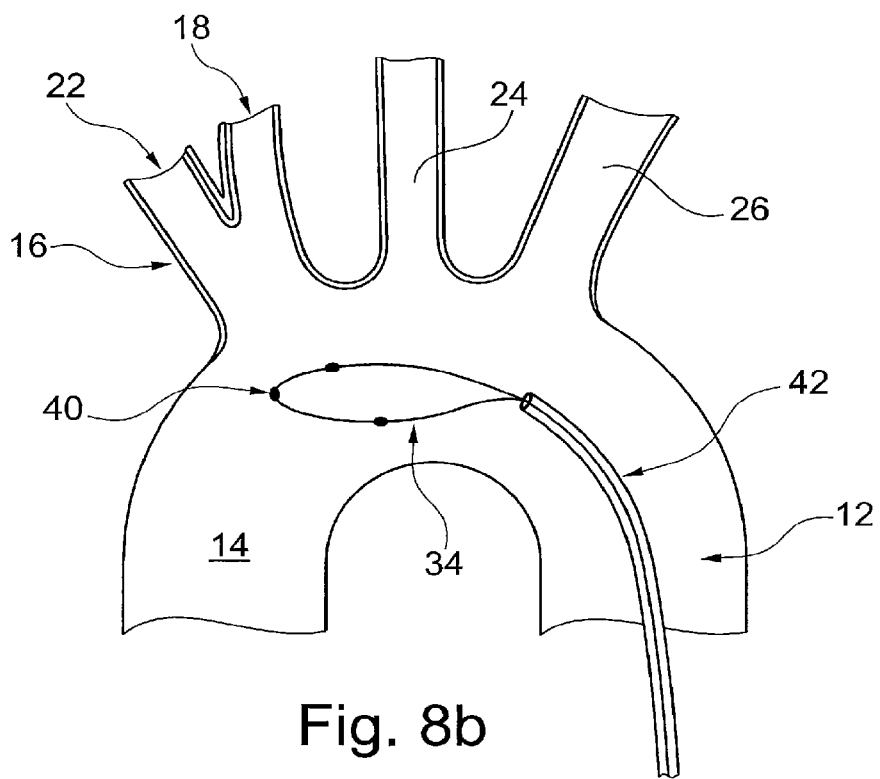
Figure 8C:
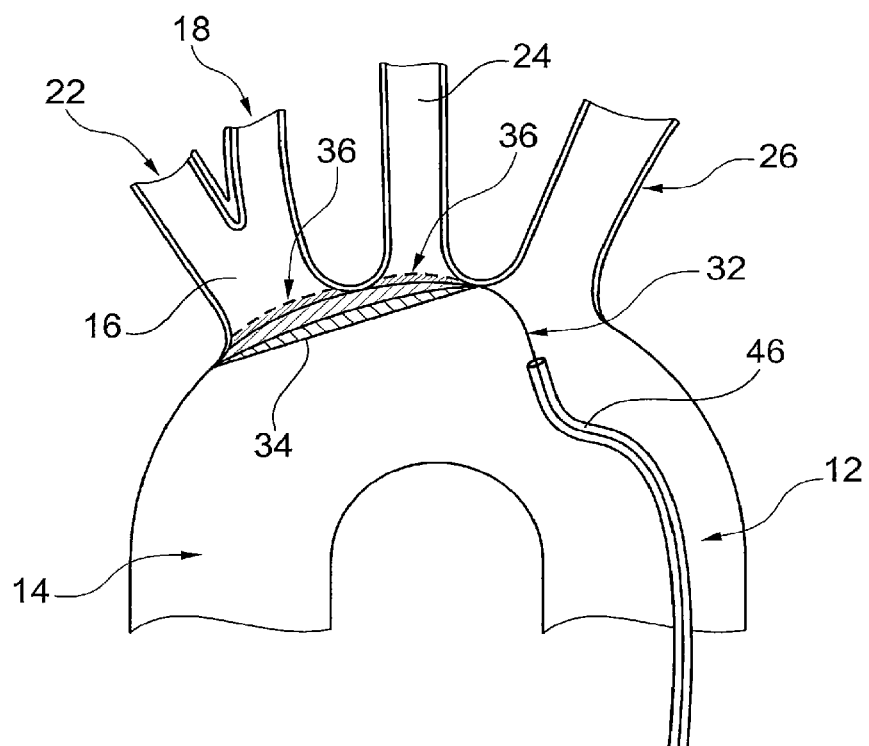
Figure 8D:
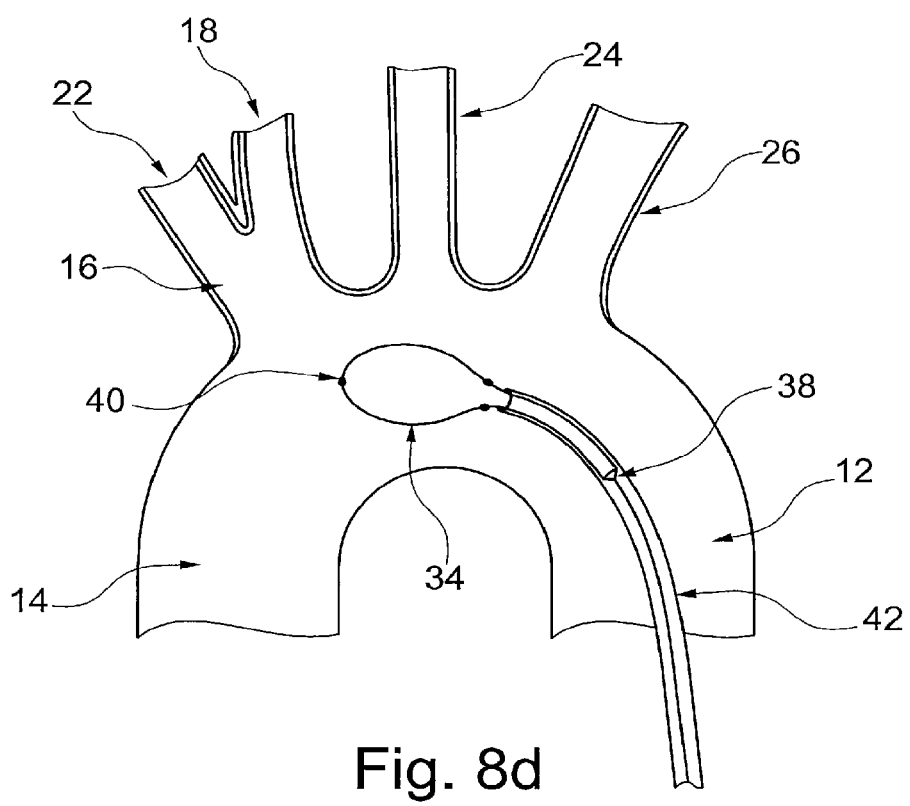

FIGS. 8a to 8d show the above described process during femoral delivery of the protective device through the descending aorta 12. The steps according to FIGS. 8a to 8d essentially correspond to the above described steps during left subclavian delivery. The only difference is shown in FIG. 8c in which the bending 46 of the distal end portion is used to position the loop frame 34 more precisely in the ostia region of the side branch vessels 16 and 24.

The invention described above, deploys via radial artery, cubital (ulnar) artery, or brachial artery approach of the left or right arm, or right or left femoral artery into the aortic arch, to cover the ostia of the side branch vessels during interventional cardiology and electrophysiology procedures, and cardiac surgery.

There are several different embodiments of the invention shown in the figures. The first embodiment of the medical device is inserted through an artery of the left arm or through the right or left femoral artery, and covers with the filter membrane the ostia of the brachiocephalic trunk and left common carotid artery, and also provides a significant protection blockage against the entrance of embolic particles to the left subclavian artery and side branch vessels mainly to the left vertebral artery with the delivery catheter placed on the lumen of the left subclavian artery (FIG. 3). The medical device according to its second embodiment is inserted through an artery of the left arm and covers with the filter membrane the ostia of the brachiocephalic trunk and the left common carotid artery. Its basket-shaped filter positioned inside the left subclavian artery protects the side branch vessels (mainly left vertebral artery) from the potential embolization with microparticles and debris (FIG. 4). The third embodiment of the protective device is inserted through an artery of the right arm and covers with the filter membrane the ostia of the left common carotid artery and the left subclavian artery. Its basket-shaped filter positioned inside the brachiocephalic trunk, protects the right carotid artery and right subclavian artery with its side branch vessels (mainly right vertebral artery) from the potential embolization with microparticles and debris (FIG. 5). The femoral delivery of the fourth embodiment is shown in FIGS. 8a to 8d. The fourth embodiment is similar to the first embodiment, however due to its femoral delivery the dimension may differ between the first and the fourth embodiment.

The purpose of the device is to provide complete cerebral protection of the entire cerebral vascular bed from embolic debris that are generated during medical procedures carried out in the aorta, heart valves, and/or heart while allowing blood flow to the brain through these arteries.

The device is intended to be fully collapsed into a 6 French sheath, and then advanced through the sheath until it deploys in the aorta and the filter membrane being positioned in the aortic arch for deflection, and the filter being positioned in the left subclavian artery for filtering and collecting emboli.

The filter membrane is slightly preshaped with a concave form to obtain better adaptation to the anatomy of the aortic arch. The mesh of the filter membrane is made of an elastic and atraumatic material that allows protruding or entering slightly inside the side branch vessels, ensuring complete sealing of its ostia without damaging the endothelium of the protected arteries.

The catheter comprises an active system for deflecting the distal end portion of the catheter into a hoop configuration having an angled position in a range of 0° to 270° allowing complete approach and contact of the mesh with the ostia of the side branch vessels, and at the same time, holding the protective position of the protective device. In the alternative or in addition the elongated shaft of the device can be provided with bending means. The shaft will be provided at its distal end of microactuators crimped to the copper contacts or other suitable material for remote actuation made of Nitinol®, steel, or other suitable material, coated with parylene or with other suitable material, by means of chemical vapor deposition or by other suitable method. This feature will improve the sealing efficiency and provide an active system for deflecting the distal portion of the shaft, ensuring complete covering and no space in between the membrane of the device and the ostia of the side branch vessels. In a preferred embodiment a coil spring or a helical spring extends around the elongated shaft and is electrically connected to microactuators by means of copper contacts to provide bending of the shaft. Contacts might be made of copper or other suitable material. Preferable the spring is covered by parylene or another flexible material.

A preferred embodiment of the frame loop is made of a shape memory material, in particular of Nitinol®. The Nitinol® frame is built from a single laser-cut piece of material. The frame can also be built from stainless steel, or from separate wires that are formed and welded together. The frame is preshaped having a slightly concave form so that it is intentionally bent back to press against the aortic wall when it is deployed acquiring the anatomical form of the aortic arch. The Nitinol® memory capacity allows the complete refolding of the frame within the delivery catheter once the procedure is completed. When laid flat, the frame measures may range from 55 mm along its longitudinal axis and 35 mm of width to ensure coverage of both left common carotid artery and brachiocephalic trunk when being delivered via an artery of the left arm or right or left femoral artery, or to ensure coverage of both left common carotid artery and left subclavian artery when being delivered via an artery of the right arm, and over a wide range of anatomies. It also could be made of different sizes ranging from 20 mm to 80 mm length, preferable 30 mm to 70 mm length and 15 mm to 60 mm width, preferable 25 mm to 50 mm width and in prespecified sizes according to anatomy and size of the aortic arch. The thickness of the frame is uniform along the entire frame and may be from the range of 0.016 inches to 0.050 inches. It may also vary in order to provide varying stiffness as needed.

The shape of the expanded frame is in general of oval form and may be symmetric to an axis extending through a center of the frame or not. In the alternative the frame may also comprise a polygonal structure with rounded corners.

The deploy sequence emanates from the most distal portion of the frame or frame tip and continues to the most proximal portion of the frame or frame base, which is connected to the shaft in the connection point. The collapse sequences emanate from the most proximal portion of the frame and continue to the most distal portion of the frame until it is completely folded into the delivery catheter.

The frame displays four radiopaque markers to ensure visibility and easy positioning of the protective device. The markers are disposed one on the most distal portion of the frame or frame tip, other on the most proximal portion of the frame or frame base, and one of each side of the frame. The markers may be made of tantalum, platinum, palladium, or other radiopaque material suitable for that purpose. Also may be more or less than 4 markers. The frame will acquire the slightly concave shape by means of thermal treatment or by other suitable method, and is attached to the most distal part of the distal end of the frame shaft and in the connection point by crimping, gluing, welding, dip-coating process, or other suitable processes. The connection point can also be formed as the point in which the frame shaft continues into the frame loop without a specific connection or attachment in this point. The radiopaque markers disposed on the frame may be plated to the frame surface, may be painted thereon, dyed, and applied as a wire wrap or coil, or any other suitable radiopaque technique. The position of the markers may be offset from the major axis of the frame to permit proper folding of the frame. Alternatively, the entire frame may be formed by injection molding, cold forming, casting, or any other suitable method, or combination of methods, or the frame may be formed to assume the desired conformation upon inflation, heating, cooling, or exposure to body fluids.

The filter membrane is a single piece membrane with calibrated micropores as active deflector of emboli that allows for blood flow but deflects microparticles of critical size away from the cerebral circulation. The membrane is provided of pores through a process of 3D laser micro-perforation on its entire length, of pores with a diameter of 80 microns, being all the same size and with a constant distance between them. Alternatively, the pore size may range from 20 microns to 200 microns and can be displaced with different distances among them, with either uniform or non-uniform pore sizes and areal distributions and patterns. The membrane can alternatively be a woven net made of PDMS or other polymer. The membrane is made of Siloxane (PDMS, Poly-dimethyl siloxane)-CH3[Si(CH3)2O]nSi(CH3)3—a polymer with non-sticky properties, hydrophobic, and highly flexible and elastic, giving the possibility of folding, unfolding and refolding within a low profile catheter. Also, the membrane may be formed from other polymer, or materials including, but not limited to PET, PETE, PETN, PTFE, EPTFE, FEP, Goretex™, Biomer™, and may be optionally filled or coated with a radiopaque material, and may be woven, airlaid, or film-formed. The membrane may be heparin coated, coated with another substance or uncoated. The membrane in its entirety have a formation divided into two portions: the first portion, constituted by the first 20% to 40% of the periphery or outer portion of the membrane will have a greater thickness of between 1.5 to 3 times more than the 80%-60% of the remaining central or inner portion of the membrane (second portion). This will allow the membrane having sufficient strength and resistance at its inner and its outer portions in contact with the aortic wall and, in turn, in the inner portion, is thin and flexible to protrude slightly into the ostia of the aortic arch vessels without damaging it. The membrane may have a thickness ranging from 20 microns to 400 microns in its thinner portion, and form 40 microns to 800 microns in its thicker portion. The membrane may be connected to the frame by dip-coating process, by crimping, or by means of other similar processes.

The shaft of the embolic protection device is made of a solid Nitinol® wire or of stainless steel, which both give flexibility and strength. Alternatively, the shaft may be made of other materials, such as platinum-chromium alloy, cobalt-chromium alloy, among others. The shaft may have a length ranging from 90 cm to 140 cm to allow for manipulation through sheaths as long as 90 cm, but also may be of different length. It has a sized ranging from 0.025 inches to 0.050 inches. The shaft may be provided with a handle disposed at its distal end, or may have microactuators crimped to the copper contacts for remote actuation made of Nitinol®, steel, or other suitable materials, coated with parylene or with other suitable materials, by means of chemical vapor deposition or by other suitable methods. This feature will provide an active system for deflecting the distal portion of the shaft. The active actuation of the shaft may be used additionally or in alternative to the bending of the distal end portion of the shaft. The deflectable length of the shaft may be in a range of 2 cm to 6 cm, and the deflectable angle may be in the range of 0° to 270°, preferable 180°. The deflection movement may be controlled manually by an electric or mechanical controller or knob or a similar method, placed in the proximal portion of the shaft.

There is disclosed a porous emboli deflector for preventing cerebral emboli while maintaining cerebral blood flow during an endovascular or open surgical procedure. The device prevents the entrance of emboli of a size able to cause stroke (such as greater than 80 microns) from entering either the right or left common carotid arteries, and/or the right or left vertebral arteries by deflecting or diverting and collecting particles dislodged or generated during a surgical procedure downstream of these vessels.

The deflector system can be placed prior to any manipulation of the heart or aorta allowing maximal protection of the brain during the index procedure, protecting the cerebral vasculature during a cardiac valve repair or replacement procedure, open heart surgery, coronary artery interventions, structural heart procedures, and catheter ablation procedures. The deflector has a low profile within the aorta which allows sheaths, catheters, or wires used in the index procedure free passage through the aortic arch. The protective device can be introduced in a 6 French access port by the arteries of the left or right arms and legs, providing multiple vascular access options.

The preferred delivery catheter is a 6 French catheter tube that allows bringing the protective device into the aortic arch, but also may be in the range of 5 French to 8 French of diameter. The delivery catheter may be a diagnostic or guiding catheter normally used for coronary or carotid interventions, such as Multipurpose catheter, Hockey-stick catheter, Amplatz left catheter, Judkins right catheter, left internal mammary artery catheter, Easy radial left long tip catheter, or may be a catheter designed specifically for this purpose. The delivery catheter may be provided of an active system for deflecting its distal portion. The deflectable length of the delivery catheter may be in a range of 2 cm to 6 cm, and the deflectable angle may be in the range of up to 270°, preferable 180°. The deflection movement may be controlled manually by an electric or mechanical controller or knob or a similar method device, placed in the proximal portion of the delivery catheter.

A vascular introducer or access port is a blunt-tipped 6 French introducer sheath with a soft atraumatic tip and distal hydrophilic coating, that allows the introduction of the delivery catheter with the protective device and can be placed in the radial artery, cubital (ulnar) artery, and brachial artery of the left or right arm, and in the left or right femoral artery. The sheath may have a length of a range from 15 cm to 45 cm.

Having described preferred embodiments of the invention, it will be apparent to those skilled in the art to which this invention relates, that modifications and amendments to various features and items can be effected and yet still come within the general concept of the invention. It is to be understood that all such modifications and amendments are intended to be included within the scope of the present invention.

What is claimed is:

1. A medical device for embolic protection in an aortic arch, comprising:
    a catheter having a shaft and a distal end portion of the shaft;
    an expandable embolic protection device having a filter membrane and a frame, wherein said frame comprises a frame loop and an elongated frame shaft having a distal end portion connected to the frame loop at a connection point, wherein in an expanded state, the frame loop spans said filter membrane; and
    a deployable filter device, which in a deployed state, extends circumferentially around said elongated frame shaft or a distal end portion of the catheter,
    wherein when said embolic protection device is expanded, said elongated frame shaft extends in a longitudinal direction of the distal end portion of the catheter and said expanded frame loop is completely positioned distally of said connection point.

2. The medical device according to claim 1, wherein in a protective state, the deployable filter device has a diameter in the deployed state such that a brachiocephalic trunk and/or a left subclavian artery can be covered tightly.

3. The medical device according to claim 1, wherein said filter membrane is a porous membrane.

4. The medical device according to claim 1, wherein said filter membrane comprises a polymer material.

5. The medical device according to claim 1, wherein the embolic protection device comprises a closed frame loop.

6. The medical device according to claim 1, wherein said frame loop carries the filter membrane.

7. The medical device according to claim 1, comprising radiopaque markers.

8. The medical device according to claim 1, wherein the frame comprises stainless steel.

9. The medical device according to claim 1, wherein the frame comprises separate wires that are formed and welded together.

10. The medical device according to claim 1, wherein the frame comprises shape memory alloy.

11. The medical device according to claim 1, wherein the catheter shaft is provided with the deployable filter device, wherein the filter membrane is of a tapered shape with its end open towards the aortic arch and wherein the deployable filter device is positioned into a left subclavian artery.

12. A method of positioning the medical device according to claim 1 in the aortic arch such that the filter membrane covers an ostia region of side branch vessels.

13. A method comprising:
    introducing an embolic protection device into a patient's aortic arch, wherein the embolic protection device comprises:
        an expandable frame supporting a filter membrane, wherein the frame comprises a frame loop to which the filter membrane is connected partially or completely by surrounding a periphery of the frame loop which is configured to engage an interior wall of the patient's aortic arch to support the embolic protection device within the patient's aortic arch and to cover an ostia of a brachiocephalic trunk and a left common carotid artery; and a deployable filter device, which in a deployed state, extends circumferentially around an elongated frame shaft or a distal end portion of a catheter.

* * * * *